US005760253A

United States Patent [19]

Danner et al.

[11] Patent Number: 5,760,253
[45] Date of Patent: Jun. 2, 1998

[54] CATALYTIC CONVERTER AND METHOD FOR HIGHLY EXOTHERMIC REACTIONS

[75] Inventors: Jeffrey B. Danner, Kennett Square; John C. Jubin, Jr.; Richard J. Wolff, both of West Chester, all of Pa.

[73] Assignee: Arco Chemical Technology, L.P., Greenville, Del.

[21] Appl. No.: 791,796

[22] Filed: Jan. 29, 1997

[51] Int. Cl.$^6$ .................................................. C07D 301/19
[52] U.S. Cl. ............................................................. 549/529
[58] Field of Search ............................................. 549/529

[56] References Cited

U.S. PATENT DOCUMENTS

| 3,109,864 | 11/1963 | Fox et al. |
| 3,351,635 | 11/1967 | Kollar. |
| 3,829,392 | 8/1974 | Wulff. |
| 3,923,843 | 12/1975 | Wulff. |
| 4,021,454 | 5/1977 | Wulff et al. |
| 4,367,342 | 1/1983 | Wulff et al. |

FOREIGN PATENT DOCUMENTS

| 0323663 | 7/1989 | European Pat. Off. |
| 1249079 | 10/1971 | United Kingdom. |

*Primary Examiner*—C. Warren Ivy
*Assistant Examiner*—Lyman H. Smith
*Attorney, Agent, or Firm*—Stephen D. Harper; William C. Long

[57] ABSTRACT

A reactor and process is for the production of oxirane compounds by reaction of an olefin such as propylene with an organic hydroperoxide using a solid contact catalyst, characterized by the following features:

(1) the reactor is divided into a series of separate zones, each zone containing a bed of solid epoxidation catalyst;

(2) about 25–75% of the heat of reaction is removed by preheating cold reactor feed by direct contact with a heated recycle stream from the reactor; and (3) about 25–75% of the heat of reaction is accounted for by a reaction mixture temperature rise of 20°–100° F. and by vaporization of 15–40% of the net reactor product.

5 Claims, 4 Drawing Sheets

5,760,253

CATALYTIC CONVERTER AND METHOD FOR HIGHLY EXOTHERMIC REACTIONS

BACKGROUND OF THE INVENTION

1. Field of the Invention

The present invention relates to a catalytic converter or reactor system and to a process for carrying out a highly exothermic reaction such as that between an olefin and an organic hydroperoxide to form an oxirane compound.

2. Description of the Prior Art

Substantial difficulties are encountered in carrying out highly exothermic reactions where reactants and/or products are temperature sensitive. For example, the catalytic liquid phase reaction of propylene and an organic hydroperoxide to produce propylene oxide is a highly exothermic reaction, and selectivity to the desired product is very temperature sensitive. Removal of the exothermic heat of reaction without causing excess temperature rise presents a serious problem.

Conventional reactors for exothermic reactions are usually of two types:

(1) Quench type which consist of multiple fixed beds with cold feed quench injected in between beds
(2) Tubular type in which the catalyst is placed in the tubes of a vertical shell and tube heat exchanger If the heat of reaction is high, the first type does not provide sufficient heat removal. This can be overcome by recycling cold reactor effluent but this results in the disadvantages associated with back-mixed reactors.

The tubular reactor cost becomes prohibitive when high heats of reaction have to be removed through heat exchanger surfaces operating with a low heat transfer coefficient. There is also a temperature gradient from the center of the tube which is often detrimental to a process which requires nearly isothermal conditions.

European Patent 0 323 663 describes a fixed bed catalytic reactor and process for carrying out the epoxidation of an olefin by reaction with an organic hydroperoxide at substantially isothermal conditions. As described in this European Patent, all heat generated by the exothermic reaction is removed by vaporization of the low boiling reaction mixture component, propylene in the case of a propylene/organic hydroperoxide system. Sufficient propylene is fed to the reactor to remove all of the reaction exotherm, and the reactor is operated at the boiling pressure of the reaction mixture in such a manner as to provide a cocurrent downflow of a liquid and a gas phase. The procedure is said to represent an improvement over the then currently employed methods involving a multi-reactor discipline with interstage cooling.

The procedure and apparatus described in European Patent 0 323 663 have a number of severe disadvantages. Where the reaction exotherm is removed by vaporization of propylene as required in the European Patent, excessive amounts of propylene must be fed as liquid to the system. In fact, the European Patent shows feeding 16.67 moles of propylene per mole of ethyl benzene hydroperoxide to the reactor which necessarily involves recovery and recycle of large volumes of propylene at great expense.

Additionally, although European Patent 0 323 663 appears to describe reactor outlet pressure of 26 bar (about 377 psi), this would not appear consistent with the vapor pressure of the liquid reaction mixture. More likely, the actual outlet pressure would be 150 psi or less and this results in an additional and very important problem which is the requirement for refrigeration and/or recompression of the great propylene recycle stream.

A further problem with the system of European Patent 0 323 663 is the poor reaction selectivity which would result at the low propylene concentrations in the liquid phase in the lower part of the reactor.

BRIEF DESCRIPTION OF THE INVENTION

In accordance with the invention, a reaction system and process is provided which is especially useful for the production of oxirane compounds by reaction of an olefin such as propylene with an organic hydroperoxide using a solid contact catalyst, the invention being characterized by the following features:

(1) the reaction is carried out in a plurality of separate reaction zones;
(2) about 25–75% of the total heat of reaction (reaction exotherm) for the system is removed by preheating cold reactor feed by direct contact of the cold feed with one or more process streams from a reaction zone;
(3) about 25–75% of the total heat of reaction (reaction exotherm) for the system is effectively removed as sensible heat in the exiting liquid and vapor streams due to a rise in the temperature of the reaction mixture to rise 20°–100° F. across the reaction system and as heat of vaporization by vaporizing 15–40 wt % of the net reactor product from the reaction system.

DESCRIPTION OF THE DRAWINGS

The attached

DETAILED DESCRIPTION

Practice of the invention is especially applicable to highly exothermic reactions such as those between an olefin, eg. propylene, and an organic hydroperoxide, eg. ethylbenzene hydroperoxide. Various important considerations associated with the present invention include:

(1) the use of a reactor system having a plurality of separate reaction zones;
(2) the provision of cold feed to the reaction system and the use of 25–75% of the system reaction exotherm to preheat the cold feed through direct contact with a stream from the reaction system; and
(3) removing the remaining 25–75% of the total heat of reaction as sensible heat in the exit streams resulting from a moderate temperature rise of 20°–100° F. of the reaction mixture during passage through the reaction system and by removing 15–40 wt % of the net reaction mixture as vapor from the reaction system. The invention can be illustrated by reference to the specific embodiment presented in the attached FIG. 1. With reference to the production of propylene oxide by reaction of propylene and ethylbenzene hydroperoxide, a relatively cold liquid feed (eg. 100° F.) comprised of ethylbenzene oxidate, ie. ethylbenzene, 1-phenyl ethanol and ethylbenzene hydroperoxide is fed via line 2 as well as propylene which is fed via line 3 to contact zone 1. By cold feed is meant feed which is 50°–150° F. below reaction temperature. Also fed to zone 1 via lines 4 and 12 in this embodiment is recycled propylene vapor from reactor 5 which was vaporized by and contains exothermic heat of reaction from the epoxidation reaction in reactor 5, zones 8 and 10.

In the embodiment described, two reactors, reactors 5 and 15, are employed, each having two reaction zones packed with solid epoxidation catalyst.

Contact zone 1 is a conventional vapor liquid contact zone suitably having several sieve trays whereby the vapor and liquid streams are intimately admixed. By this contact and mixing, exothermic reaction heat which resulted in vaporization of propylene in reactor 5 is used to heat the relatively cold feed components to reaction temperature. In the process, most of the propylene vapor from reactor 5 is condensed. As a result of this heat exchange, 25–75% of the total system exotherm is effectively removed and used to preheat the cold feed streams.

Figure 2A:
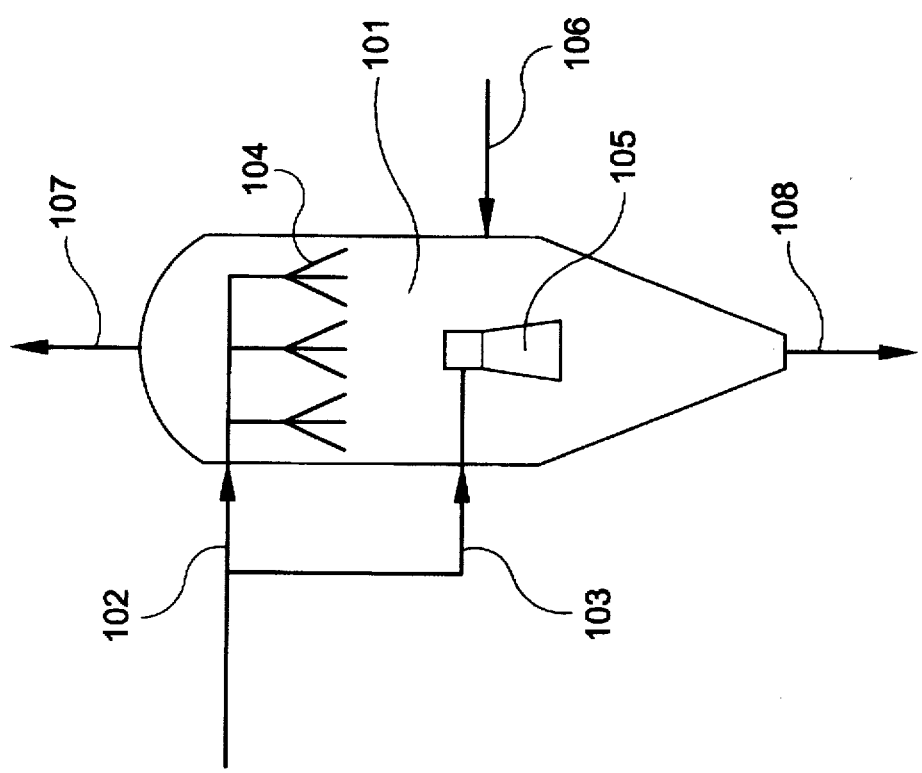
FIGS. 2a and 2b illustrate cold feed preheat methods.
Figure 2B:
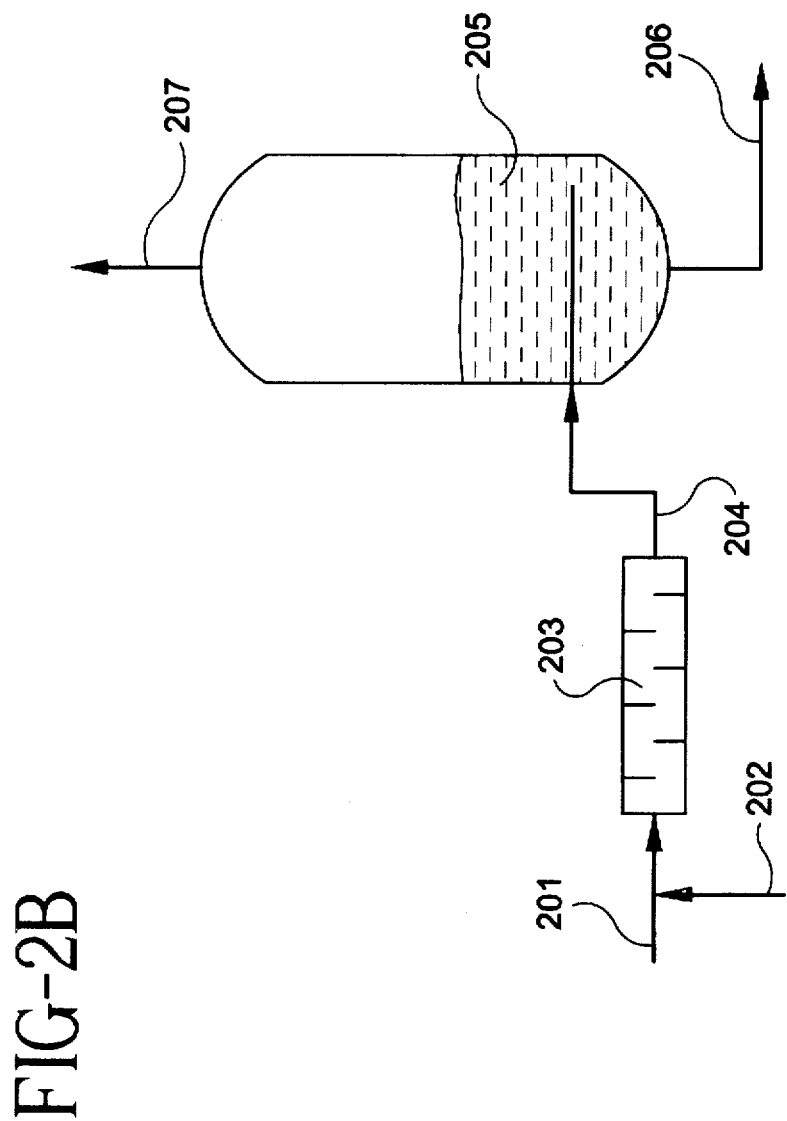

Alternate configurations for zone 1 are shown in FIGS. 2a and 2b. In FIG. 2a, the contacting is achieved by spraying the cold liquid feed into the vessel receiving the propylene vapor. A portion of the liquid is introduced as a jet to increase the pressure of the condensed liquid. In FIG. 2b, contacting is achieved mainly by a "static mixer". Additional contacting is achieved by introducing the vapor liquid mixture below the liquid level. Economics will dictate the optimum for a particular practice.

From contact zone 1, the heated liquid mixture is pumped via line 6 to upper zone 7 of reactor 5. If the heat available from the propylene vapor streams is not sufficient to heat the liquid mixture quite to reaction temperature, supplemental heat can be provided by heater 24 which in any event is useful during start up.

From upper zone 7, the liquid reaction mixture passes at reaction conditions through zone 8 which contains a packed bed of titania on silica catalyst prepared as described in Example VII of U.S. Pat. No. 3,923,843 the disclosure of which is incorporated herein by reference. During passage through the catalyst bed in zone 8 the exothermic reaction of propylene with ethylbenzene hydroperoxide takes place with the formation of propylene oxide.

As a result of the reaction exotherm in zone 8, there is a modest rise in temperature of the reaction mixture, eg. 10°–40° F. In addition, the remaining reaction exotherm is consumed by vaporization of the propylene component of the reaction mixture.

The reaction mixture passes through the solid catalyst in zone 8 to separation zone 9 wherein liquid and vapor components are separated. Propylene vapor is removed via line 4 and passes to contactor 1 wherein, as above described, the vapor is used to preheat the cold reaction feed.

The liquid reaction mixture passes from separation zone 9 to zone 10 which is also packed with the titania on silica catalyst used in zone 8. In zone 10 further exothermic reaction of propylene with ethylbenzene hydroperoxide takes place to form propylene oxide.

Once again, the exothermic heat of reaction is accounted for by a modest temperature increase of the reaction mixture in zone 10 together with vaporization of propylene. The reaction mixture passes from zone 10 to separation zone 11 wherein liquid and vapor components are separated. Propylene vapor passes via line 12 to contactor 1 wherein, as above described the vapor is used to preheat the cold reaction feed.

A significant advantage of this mode of operation resides in the fact that the preponderance of propylene vapor from reactor 5 is condensed in contactor 1 and recycled to reactor 5. The use of very high propylene to hydroperoxide ratios in the reaction feed is thus avoided.

Liquid reaction mixture passes from reactor 5 via line 13. Level control means 52 is provided to insure that an appropriate liquid level is maintained. Supplemental liquid propylene can be introduced via line 50 to maintain the desired reactant ratio and the mixture of reaction liquid from reactor 5 and newly added propylene passes via line 51 to zone 14 of reactor 15 and from zone 14 into reaction zone 16 which contains a packed bed of the titania on silica catalyst used in reactor 5.

In zone 16 further exothermic reaction of propylene and ethylbenzene hydroperoxide takes place to form propylene oxide. Exotherm heat of reaction from the reaction in zone 16 is accounted for by an increase in the reaction mixture temperature of about 10°–50° F. and by vaporization of propylene.

From zone 16, the mixture passes to separation zone 17 wherein vapor and liquid are separated. Propylene vapor is removed via line 18 and the reaction liquid is passed to packed catalyst reaction zone 19 for final reaction of propylene and ethylbenzene hydroperoxide. Zone 19 contains the titania on silica catalyst used in the previous reaction zones and reaction of propylene and ethylbenzene hydroperoxide takes place therein. Exotherm in zone 19 is accounted for, as previously, by a small temperature increase and by vaporization of propylene.

The reaction mixture at a temperature 20°–100° F. higher than the temperature of the reaction mixture entering reactor 5 passes to separation zone 20 in which vapor and liquid are separated. Propylene vapor is removed via line 21 and the liquid reaction product mixture is removed via line 22.

The vapor streams removed via lines 23, 18 and 21 as well as the liquid stream removed via line 22 are sent to a distillation operation or depropanizer wherein lighter components are separated by distillation from the heavier materials in accordance with known procedures. Where appropriate light components such as propylene are recovered and recycled. In accordance with the invention, the vapor streams removed via lines 23, 18 and 21 comprise by weight 15–40% of the net reaction mixture removed ie. the sum of streams 23, 18, 21 and 22.

The heavier materials are likewise separated by conventional procedures into products as well as streams for recycle.

The embodiment of the invention has been described in the context of a two reactor system, each reactor having 2 reaction zones. The two reactors could be combined into a single apparatus, or alternatively a number of reactors greater than two can conveniently be used, if overall economics so dictate.

The use of two reactors permits the first reactor to be operated at a high pressure sufficient to return propylene vapor to the feed contactor zone 1. The second reactor can be operated at a lower pressure consistent with the optimum temperature and propylene concentration required for the final reaction phase.

As above indicated, FIGS. 2a and 2b describe alternative contact means for preheating cold feed by contact with recycle propylene vapor.

In FIG. 2a, cold feed is introduced into contact zone 101 via lines 102 and 103. The liquid introduced via line 102 is sprayed via spray nozzles 104 into zone 101 while the liquid introduced via line 103 is passed via jet 105 into zone 101. Propylene vapor is introduced via line 106 and in zone 101 the propylene vapor intimately contacts and preheats the liquid feed. Uncondensed vapor exits zone 101 via line 107 and heated feed exits via line 108.

In FIG. 2b, cold feed is introduced via line 201 and propylene vapor via line 202 to static mixing zone 203. Zone 203 has baffles which insure thorough vapor/liquid mixing. From zone 203 the mixture passes via line 204 to vessel 205 where it is preferably introduced below the liquid surface. Preheated liquid passes via line 206 to the reactor while uncondensed propylene is removed via line 207.

As will be apparent, other contact means can be employed depending upon the economics of a particular practice of the invention.

The extent to which the exothermic reaction takes place in the various reaction zones can be readily controlled. By proper regulation of reactant composition, flow rates, temperature, pressure, and catalyst contact time in a reaction zone, the reaction which takes place in that zone and hence the reaction exotherm which is generated can be suitably regulated.

In accordance with the embodiment of the present invention, as above described, about 25–75% of the total reaction exotherm is used to vaporize propylene in reaction zones 8 and 10 and this reaction exotherm is essentially used to preheat cold feed in contact zone 1, a small amount of the vapor is not condensed and is removed via line 23.

Of the remaining 25–75% of the total reaction exotherm, this is accounted for as sensible heat in the net system exit streams as a result of the modest increase in the temperature of the reaction mixture upon passage through zones 8, 10, 16 and 19 of about 20°–100° F. and as heat of vaporization by vaporization of propylene in zones 16 and 19, resulting in propylene vapor removal via lines 23, 18 and 21 comprising about 15–40 wt % of the total of the streams removed from reactor 15 via lines 23, 18, 21 and 22.

Figure 3:
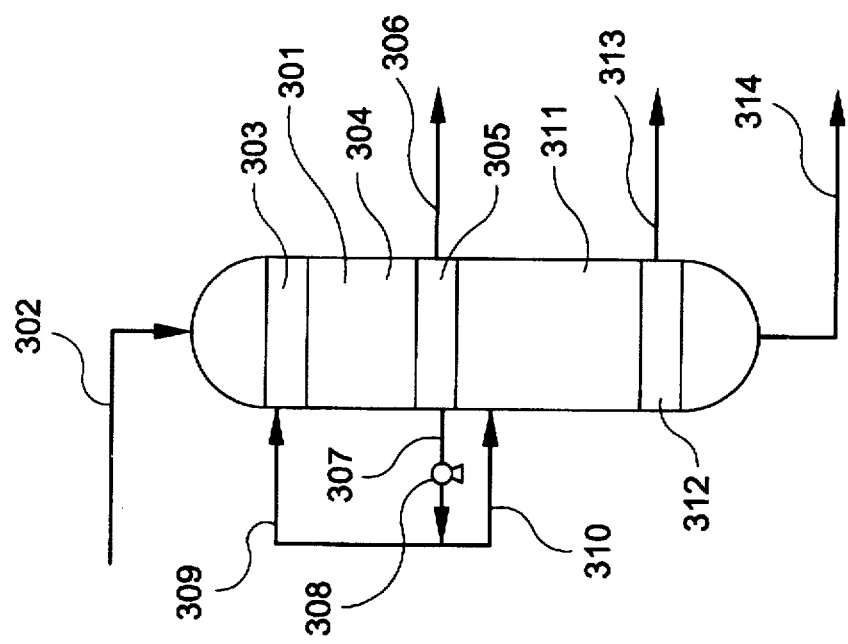
FIG. 3 illustrates an alternative practice of the invention.

An alternative practice of the invention which employs somewhat simpler equipment is illustrated in FIG. 3.

Referring to FIG. 3, there is provided reactor 301 which has two sections packed with the solid epoxidation catalyst. Cold feed comprised of ethylbenzene hydroperoxide as above described and propylene is introduced via line 302 into zone 303 wherein it is intimately mixed with a portion of the liquid reaction mixture from reactor zone 304. As a result of this contact and mixing a portion of the exothermic heat of reaction generated in zone 304 is used to preheat the cold feed to reaction temperature. The heated feed and recycle reaction liquid pass from zone 303 into zone 304 wherein they are contacted with solid epoxidation catalyst and wherein ethylbenzene hydroperoxide and propylene react to form propylene oxide. The reaction mixture passes to separation zone 305 from which propylene which is vaporized by the reaction exotherm is removed via line 306. The liquid reaction product mixture is removed from zone 305 via line 307 and pump 308 and is divided into two parts, one being recycled via line 309 to zone 303 wherein it is admixed with and preheats the cold feed as above described, and the other passing via line 310 to reaction zone 311.

Reaction zone 311 is packed with solid epoxidation catalyst and in this zone further reaction of ethylbenzene hydroperoxide and propylene takes place with formation of propylene oxide. The reaction mixture passes to separation zone 312 from which propylene vaporized by the reaction exotherm in zone 311 is removed via line 313. The liquid reaction product mixture is uncovered via line 314.

Operation of reactor 301 is controlled such that 25–75% of the total reaction heat generated in zones 304 and 311 is contained as sensible heat in the stream recycled via line 309 and used to preheat the cold feed.

The remaining 25–75% of the exotherm is removed as the heat of vaporization in the vapor streams in lines 306 and 313, and as sensible heat in the liquid mixture removed via line 314 which results from a 20–100° F. temperature rise in zones 304 and 311.

The vapor removed via lines 306 and 313 comprises 15–40 wt % of the total of the streams in lines 306, 313 and 314.

Product workup is accomplished in accordance with known procedures.

The epoxidation reaction of the present invention is carried out in accordance with well known conditions. See, for example, U.S. Pat. No. 3,351,635, the disclosure of which is incorporated herein by reference.

Generally reaction temperatures are in the range of 150° F. to 250° F., usually 180° F. to 225° F., and pressures are sufficient to maintain the liquid phase in reactor 1, eg. 500 to 800 psia.

Known solid heterogeneous catalysts are employed. In this regard, reference is made to European patent publication 0 323 663, to UK 1,249,079, to U.S. Pat. Nos. 4,367,342, 3,829,392, 3,923,843 and 4,021,454 the disclosures of which are incorporated herein.

The invention is especially applicable to epoxidation of alpha olefins having 3–5 carbon atoms with aralkyl hydroperoxide.

Figure 1:
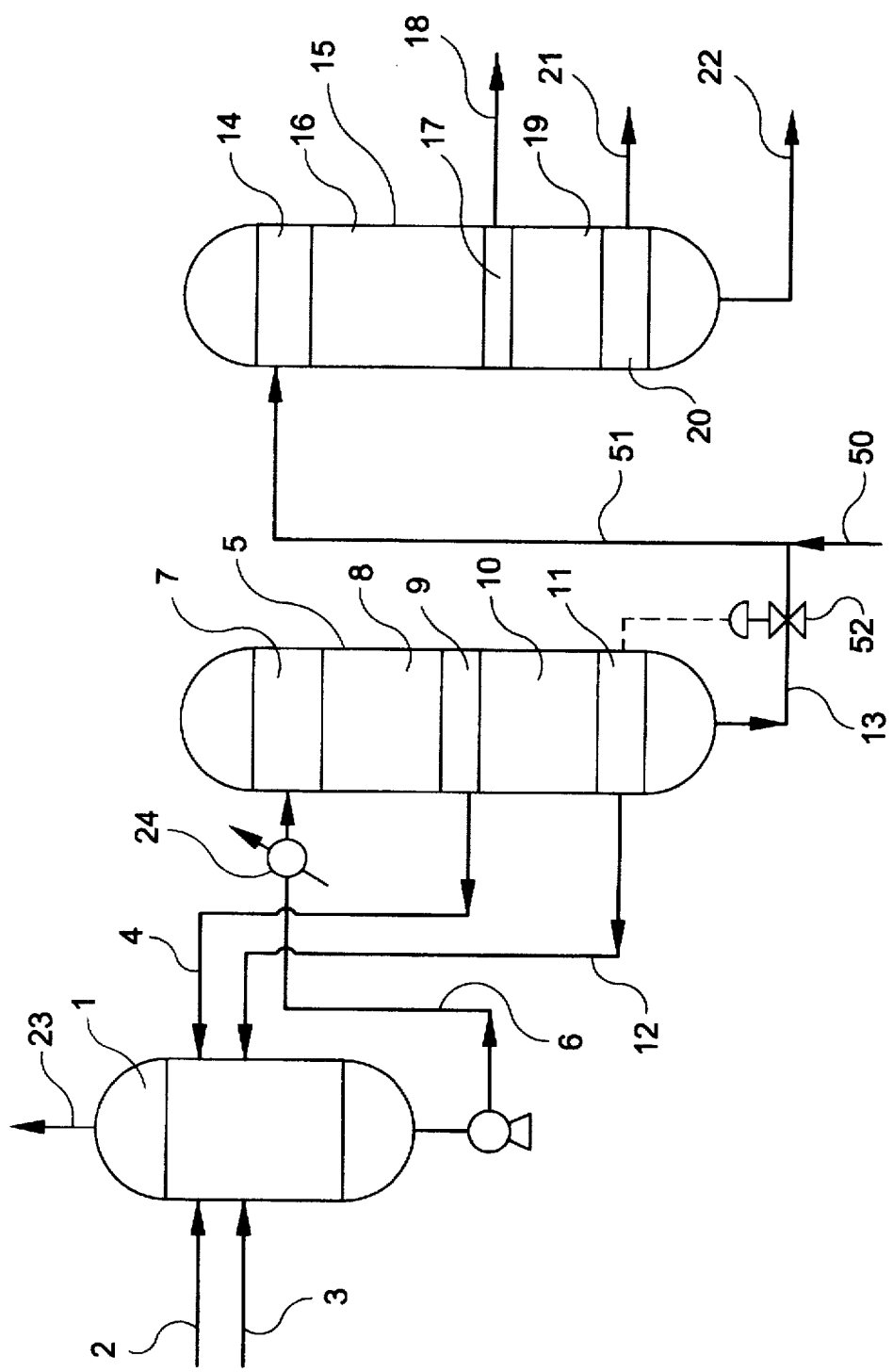
FIG. 1 illustrates a practice of the invention.

The following example illustrates an especially preferred practice of the invention as described in the accompanying FIG. 1.

Referring to FIG. 1, propylene feed at about 100° F. and 700 psia is introduced to zone 1 via line 3 at the rate of about 662 lbs/hr. Ethylbenzene oxidate also at 100° F. and 700 psia is introduced via line 2 at the rate of about 560 lbs/hr.

Also fed to zone 1 via line 4 at the rate of 512 lbs/hr and vice line 12 at the rate of 263 lbs/hr is recycled propylene vapor from reactor 5 which was vaporized by and contains exothermic heat of reaction from the epoxidation reaction in reactor 5, zones 8 and 10.

Contact zone 1 is a conventional vapor liquid contact zone suitably having several sieve trays whereby the vapor and liquid streams are intimately admixed. By this contact and mixing, exothermic reaction heat of the propylene vapor from reactor 5 is used to heat the relatively cold feed components to reaction temperature. In the process, most of the propylene vapor from reactor 5 is condensed; a vapor stream comprised of the uncondensed vapor is removed via line 23 at the rate of 125 lbs/hr and is sent to recovery.

From contact zone 1, the heated liquid mixture at 201° F. is pumped via line 6 at the rate of 1871 lbs/hr to upper zone 7 off reactor 5.

From upper zone 7, the liquid reaction mixture passes at reaction conditions through zone 8 which contains a packed bed of titania on silica catalyst prepared as described in Example VII of U.S. Pat. No. 3,923,843. During passage through the catalyst bed in zone 8 the exothermic reaction of propylene with ethylbenzene hydroperoxide takes place with the formation of propylene oxide. Pressure entering zone 8 is 730 psia.

As a result of the reaction exotherm in zone 8, there is a rise in temperature of the reaction mixture of 35° F. In addition, the remaining exotherm is consumed by vaporization of the propylene component of the reaction mixture.

The reaction mixture passes through the solid catalyst in zone 8 to separation zone 9 wherein liquid and vapor components are separated. Propylene vapor at 236° F. is removed via line 4 and passes to contactor 1 wherein, as above described, the vapor is used to preheat the cold reaction feed.

The liquid reaction mixture passes from separation zone 9 to zone 10 which is also packed with the titania on silica catalyst used in zone 8. In zone 10 further exothermic reaction of propylene with ethylbenzene hydroperoxide takes place to form propylene oxide.

The exothermic heat of reaction is accounted for by a temperature increase of the reaction mixture to 249° F. in zone 10 together with vaporization of propylene. The reaction mixture passes from zone 10 at 700 psia to separation zone 11 wherein liquid and vapor components are separated. Propylene vapor at 249° F. passes via line 12 to contactor 1 wherein, as above described the vapor is used to preheat the cold reaction feed.

The following table gives the weight percentage compositions for the various process streams. The Stream No. designation refers to the process stream in the corresponding line or zone in the attached FIG. 1.

TABLE 1

| Stream No. | Stream Composition wt % | | | | | | | | | | | |
|---|---|---|---|---|---|---|---|---|---|---|---|---|
| | 3 | 2 | 4 | 12 | 6 | 23 | 13 | 18 | 21 | 22 | 50 | 51 |
| Propylene | 90.6 | — | 83.7 | 81.8 | 60.4 | 87.1 | 40.7 | 81.9 | 81.3 | 32.9 | 90.6 | 45.9 |
| Propane | 9.14 | — | 10.8 | 10.5 | 7.2 | 11.0 | 4.7 | 10.2 | 10.0 | 3.7 | 9.4 | 5.2 |
| Ethylbenzene | — | 58.7 | 3.6 | 4.2 | 19.0 | 1.5 | 29.8 | 3.6 | 3.7 | 33.7 | — | 4.7 |
| Ethylbenzene Hydroperoxide | — | 35.0 | 0.1 | 0.1 | 10.5 | 0.05 | 5.5 | — | — | 0.4 | — | 4.9 |
| Methyl Benzyl Alcohol | — | 6.3 | 0.3 | 0.5 | 2.1 | 0.05 | 14.1 | 0.5 | 0.5 | 21.8 | — | 2.6 |
| Propylene Oxide | — | — | 1.5 | 2.9 | 0.8 | 0.3 | 5.2 | 3.8 | 4.4 | 7.4 | — | 4.7 |
| By-Product | — | — | — | — | — | — | — | — | — | 0.1 | — | — |

A significant advantage of this mode of operation resides in the fact that the preponderance of propylene vapor from reactor 5 is condensed in contactor 1 and recycled to reactor 5. The use of very high propylene to hydroperoxide ratios in the reaction feed is thus avoided.

Liquid reaction mixture from reactor 5 at 249° F., 700 psia passes via line 13 at the rate of 1097 lbs/hr through liquid level controller 52 and is admixed with 132 lbs/hr additional cold propylene feed. The resulting mixture passes at the rate of 1229 lbs/hr via line 51 to zone 14 of reactor 15 and from zone 14 into reaction zone 16 which contains a packed bed of the titania on silica catalyst used in reactor 5. In zone 14, the pressure is reduced to 600 psia which results in substantial propylene vaporization and a reduction in temperature to 225° F.

In zone 16 further exothermic reaction of propylene and ethylbenzene hydroperoxide takes place to form propylene oxide. Exotherm from the reaction in zone 16 is accounted for by an increase in the reaction mixture temperature to about 241° F. and by vaporization of propylene.

From zone 16, the mixture passes to separation zone 17 wherein vapor and liquid are separated. Propylene vapor at 241° F. removed via line 18 at the rate of 238 lbs/hr and the reaction liquid is passed to packed catalyst reaction zone 19 for final reaction of propylene and ethylbenzene hydroperoxide. Zone 19 contains the titania on silica catalyst used in the previous reaction zones and reaction of propylene and ethylbenzene hydroperoxide takes place therein. Exotherm in zone 19 is accounted for, as previously, by a small temperature increase and by vaporization of propylene.

The reaction mixture at a temperature of 243° F. and a pressure of 575 psia passes to separation zone 20 in which vapor and liquid are separated. Propylene vapor is removed via line 21 at 243° F. and 575 psia at the rate of 56 lbs/hr and the liquid reaction product mixture is removed via line 22 at 243° F. at the rate of 935 lbs/hr.

The vapor streams removed via lines 23, 18 and 21 as well as the liquid stream removed via line 22 are sent to a distillation operation or depropanizer wherein lighter components are separated by distillation from the heavier materials in accordance with known procedures. As required in accordance with the invention, the vapor streams removed via lines 23, 18 and 21 comprise about 31% by weight of the net product. Where appropriate light components such as propylene are recovered and recycled.

The heavier materials are likewise separated by conventional procedures into products as well as streams for recycle.

In this example, conversion based on hydroperoxide is 98%, and the molar selectivity of propylene to propylene oxide is 99%, thus demonstrating the efficiency and effectiveness of the invention. Costs associated with construction and operation of the system are substantially minimized.

In the above example, 50% of the reaction exotherm is used to preheat the cold feed in contact zone 1. About 18% of the reaction exotherm is accounted for by the temperature in reactor 5 and reactor 15. The remaining 32% of the exotherm is accounted for by propylene vaporization and removal of propylene vapor via lines 23, 18 and 21.

We claim:

1. In a process for the catalytic liquid phase exothermic reaction of a $C_3$–$C_5$ olefin with an aralkyl hydroperoxide which comprises passing a mixture containing the olefin and hydroperoxide at reaction conditions of elevated temperature and pressure through a series of separate reaction zones each packed with a bed of solid epoxidation catalyst, the improvement wherein (1) a reaction system is employed having a plurality of separate reaction zones, (2) cold olefin and hydroperoxide feed is provided to the reaction system and 25–75% of the reaction exotherm generated in the reaction system is used to preheat the cold feed through direct contact with a recycle stream from the reaction system, and (3) 25–75% of the reaction exotherm in the reaction system is removed as sensible heat due to a temperature rise of 20°–100° F. of the reaction mixture during passage through the reaction system and as heat of vaporization by removal of 15–40% of the net reaction mixture as vapor from the reaction system.

2. The process of claim 1 wherein propylene and ethylbenzene hydroperoxide are reacted to form propylene oxide.

3. The process of claim 1 wherein the solid catalyst is a titania on silica catalyst.

4. The process of claim 1 wherein said recycle stream in (2) is a propylene vapor stream.

5. The process of claim 1 wherein said recycle stream in (2) is a liquid reaction mixture stream.

* * * * *